US011633676B2

(12) United States Patent
Chiu et al.

(10) Patent No.: US 11,633,676 B2
(45) Date of Patent: Apr. 25, 2023

(54) PHASE SEPARATION BEHAVIOR MODIFYING AGENTS FOR AQUEOUS TWO-PHASE SEPARATION WITHIN POROUS MATERIAL

(71) Applicant: PHASE DIAGNOSTICS, INC., Garden Grove, CA (US)

(72) Inventors: Yin To Chiu, Hong Kong (HK); Brian Sangwoo Lee, La Mirada, CA (US); Garrett Lee Mosley, Hong Kong (HK); Beatrice S. Lim, Anaheim, CA (US)

(73) Assignee: PHASE DIAGNOSTICS, INC., Garden Grove, CA (US)

( * ) Notice: Subject to any disclaimer, the term of this patent is extended or adjusted under 35 U.S.C. 154(b) by 654 days.

(21) Appl. No.: 16/608,842

(22) PCT Filed: Jun. 1, 2018

(86) PCT No.: PCT/US2018/035569
§ 371 (c)(1),
(2) Date: Oct. 27, 2019

(87) PCT Pub. No.: WO2018/222972
PCT Pub. Date: Dec. 6, 2018

(65) Prior Publication Data
US 2020/0197833 A1    Jun. 25, 2020

Related U.S. Application Data

(60) Provisional application No. 62/599,001, filed on Dec. 14, 2017, provisional application No. 62/513,994, filed on Jun. 1, 2017.

(51) Int. Cl.
*B01D 17/02* (2006.01)
*C07K 1/14* (2006.01)
(Continued)

(52) U.S. Cl.
CPC ...... *B01D 17/0214* (2013.01); *B01D 11/0492* (2013.01); *B01D 15/00* (2013.01);
(Continued)

(58) Field of Classification Search
CPC . G01N 1/405; G01N 2001/4061; B01D 17/12
See application file for complete search history.

(56) References Cited

U.S. PATENT DOCUMENTS 6,132,763 A    10/2000 Fisher
6,399,385 B1    6/2002 Croyle et al.
(Continued)

FOREIGN PATENT DOCUMENTS

CN    101679481 A    3/2010
CN    102272144 A    12/2011
(Continued)

OTHER PUBLICATIONS

Frank Luechau, et al., Partition of plasmid DNA in polymer-salt aqueous two-phase systems, Separation and Purification Technology, Apr. 20, 2009, pp. 397-404, vol. 66, No. 2, Elsevier Science, Amsterdam, NL.
(Continued)

*Primary Examiner* — David Z Huang
*Assistant Examiner* — Jean F Morello
(74) *Attorney, Agent, or Firm* — Eagle IP Limited

(57) ABSTRACT

The present invention relates to a method and/or device for improving the separation behaviors and performance of aqueous two-phase system (ATPS) for the isolation and/or concentration of one or more target analytes from a sample. In one embodiment, the present method and device comprise ATPS components within a porous material and one or more phase separation behavior modifying agents that improve the separation behavior and performance characteristics of ATPS, including but not limited to the increasing the sta-
(Continued)

Blank

Uniform

Partial

Gradient

Mixed bility or reducing fluctuations of ATPS thought the adjustment of total volume of a sample solution that undergoes phase separation, volume ratio of the two phases of the ATPS, fluid flow rates, and concentrations of ATPS components.

20 Claims, 2 Drawing Sheets

(51) Int. Cl.
    *C07K 1/36*     (2006.01)
    *B01D 15/00*     (2006.01)
    *B01J 20/32*     (2006.01)
    *G01N 1/40*     (2006.01)
    *B01D 19/00*     (2006.01)
    *B01D 11/04*     (2006.01)
    *B01D 17/12*     (2006.01)

(52) U.S. Cl.
    CPC ......... *B01D 17/02* (2013.01); *B01D 17/0202* (2013.01); *B01D 17/12* (2013.01); *B01D 19/0057* (2013.01); *B01J 20/3208* (2013.01); *B01J 20/3274* (2013.01); *B01J 20/3287* (2013.01); *B01J 20/3289* (2013.01); *C07K 1/145* (2013.01); *C07K 1/36* (2013.01); *G01N 1/405* (2013.01); *G01N 2001/4061* (2013.01)

(56) References Cited

U.S. PATENT DOCUMENTS

| | | |
|---|---|---|
| 7,626,017 B2 | 12/2009 | Laugharn, Jr. et al. |
| 7,666,583 B2 | 2/2010 | Mor et al. |
| 7,803,405 B2 | 9/2010 | Keating et al. |
| 9,823,247 B2 | 11/2017 | Kamei et al. |
| 10,006,911 B2 | 6/2018 | Kamei et al. |
| 10,359,423 B2 | 7/2019 | Kamei et al. |
| 10,578,616 B2 | 3/2020 | Kamei et al. |
| 11,287,426 B2 | 3/2022 | Kamei et al. |
| 11,327,075 B2 | 5/2022 | Kamei et al. |
| 2002/0042506 A1 | 4/2002 | Kristyanne et al. |
| 2005/0077497 A1 | 4/2005 | Anderson |
| 2006/0025579 A1 | 2/2006 | Riedl et al. |
| 2006/0166349 A1 | 7/2006 | Kepka et al. |
| 2007/0161000 A1 | 7/2007 | Van Alstine et al. |
| 2008/0242825 A1 | 10/2008 | Devi et al. |
| 2009/0192111 A1 | 7/2009 | Bader et al. |
| 2009/0286966 A1 | 11/2009 | Christensen et al. |
| 2010/0174052 A1 | 7/2010 | Hjorth et al. |
| 2010/0179252 A1 | 7/2010 | Johansson et al. |
| 2011/0257378 A1 | 10/2011 | Tran et al. |
| 2011/0263040 A1 | 10/2011 | Jones |
| 2013/0164825 A1 | 6/2013 | Gabriele et al. |
| 2014/0221549 A1 | 8/2014 | Bodkhe et al. |
| 2014/0227712 A1 | 8/2014 | Horlitz et al. |
| 2014/0228549 A1 | 8/2014 | Bernhard et al. |
| 2015/0253320 A1 | 9/2015 | Kamei et al. |
| 2018/0100854 A1 | 4/2018 | Kamei et al. |
| 2018/0259521 A1* | 9/2018 | Kamei ............... G01N 33/558 |
| 2019/0033308 A1 | 1/2019 | Kamei et al. |
| 2019/0187140 A1* | 6/2019 | Kamei .................. G16H 30/40 |
| 2019/0250156 A1* | 8/2019 | Kamei ............... G01N 33/543 |
| 2019/0391143 A1 | 12/2019 | Kamei et al. |
| 2020/0150116 A1* | 5/2020 | Kamei ............ G01N 33/56988 |
| 2020/0284791 A1 | 9/2020 | Kamei et al. |
| 2022/0252598 A1 | 8/2022 | Kamei et al. |

FOREIGN PATENT DOCUMENTS

| | | |
|---|---|---|
| CN | 102421898 A | 4/2012 |
| CN | 106662582 A | 5/2017 |
| CN | 110003323 A | 7/2019 |
| EP | 0268946 A2 | 6/1988 |
| JP | 2000245460 A | 9/2000 |
| JP | 2002537106 A | 11/2002 |
| JP | 2007525222 A | 9/2007 |
| JP | 2017513015 A | 5/2017 |
| WO | 0050161 A1 | 8/2000 |
| WO | 2002057289 A1 | 7/2002 |
| WO | 2011159537 A2 | 12/2011 |
| WO | 2014128129 A1 | 8/2014 |
| WO | 2015134938 A1 | 9/2015 |
| WO | 2016155888 A1 | 10/2016 |
| WO | 2017041030 A1 | 3/2017 |
| WO | 2017214315 A1 | 12/2017 |
| WO | 2018039139 A1 | 3/2018 |
| WO | 2018183454 A1 | 10/2018 |
| WO | 2018183465 A1 | 10/2018 |
| WO | 2018222972 A1 | 12/2018 |
| WO | 2019046553 A1 | 3/2019 |
| WO | 2019046563 A1 | 3/2019 |
| WO | 2019055926 A2 | 3/2019 |
| WO | 2019118712 A1 | 6/2019 |
| WO | 2019143895 A1 | 7/2019 |
| WO | 2019143943 A2 | 7/2019 |
| WO | 2019144016 A1 | 7/2019 |
| WO | 2019144030 A1 | 7/2019 |

OTHER PUBLICATIONS

Vijayaragavan K. Saagar et al., Separation of porcine parvovirus from bovine serum albumin using PEG-salt aqueous two-phase system, Journal of Chromatography B, Sep. 1, 2014, pp. 118-126, vol. 967, NL.

Erik Jue et al., Using an aqueous two-phase polymer-salt system to rapidly concentrate viruses for improving the detection limit of the lateral-flow immunoassay: Concentrating Viruses in a Polymer-Salt System, Biotechnology and Bioengineering, Dec. 1, 2014, pp. 2499-2507, vol. 111, No. 12, US.

Paz Sean et al., A simplified SARS-CoV-2 detection protocol for research laboratories, Plos One, Dec. 18, 2020, p. e0244271, vol. 15, No. 12.

Ziegler YS, et al. (2014) Plasma membrane proteomics of human breast cancer cell lines identifies potential targets for breast cancer diagnosis and treatment. PLoS One. 9(7):e102341.

Schindler J, et al. (2008) Aqueous polymer two-phase systems for the proteomic analysis of plasma membranes from minute brain samples. J Proteome Res 7(1):432-442.

Spindler KL, et al. (2015) Circulating free DNA as biomarker and source for mutation detection in metastatic colorectal cancer. PLoS One.10(4):e0108247.

Riedl W, et al. (2008) Membrane-supported extraction of biomolecules with aqueous two-phase systems[J]. Desalination, 224(1-3): 160-167.

Frerix A, et al. (2005) Scalable recovery of plasmid DNA based on aqueous two-phase separation. Biotechnol Appl Biochem. 42(Pt 1):57-66.

Crucho CIC, et al. (2017) Polymeric nanoparticles: A study on the preparation variables and characterization methods. Mater Sci Eng C Mater Biol Appl. 80:771-784.

Shin H, et al. (2015) High-yield isolation of extracellular vesicles using aqueous two-phase system. Sci Rep. 5:13103.

Zeringer E, et al. (2015) Strategies for isolation of exosomes. Cold Spring Harb Protoc. (4):319-323.

Iqbal M, et al. (2016) Aqueous two-phase system (ATPS): an overview and advances in its applications. Biol Proced Online. 18:18.

Zhou et al. (2015) Nanoparticle Vesicles with Controllable Surface Topographies through Block Copolymer-Mediated Self-Assembly of Silica Nanospheres, Langmuir, vol. 31(48), 11 pp. 13214-13220.

Bashir et al. (2016) Controlled-release of Bacillus thurigiensis formulations encapsulated in light-resistant colloidosomal microcapsules for the management of lepidopteran pests of *Brassica* crops, PEERJ., vol. 4(e2524). pp. 1-14.

Sigma-Aldrich "Poly(ethylene glycol) octyl ether" Retrieved from the Internet <URL:https://www.google.com/search?q=poly%28ethylene+glycol%29+octyl+ether&source=lnt&tbs=cdr%3A1%

(56) References Cited

OTHER PUBLICATIONS

2Ccd_min%3A%2Ccd_max%3A1%2F18%2F2018&tbm=> <URL https://www.sigmaaldrich.com/catalog/product/sigma/40530?lang=en&region=US> [retrieved on Jun. 16, 2020].

Luechau, Frank; et al. (2009) Primary capture of high molecular weight nucleic acids using aqueous two-phase systems. Separation and purification technology, 66.1: 202-207.

Nazer, Behzad; et al. (2017) Plasmid DNA affinity partitioning using polyethylene glycol-sodium sulfate aqueous two-phase systems. Journal of Chromatography B, 1044:112-119.

Sorber L, et al. (2017) A Comparison of Cell-Free DNA Isolation Kits: Isolation and Quantification of Cell-Free DNA in Plasma. J Mol Diagn. Jan.;19(1):162-168.

Steven B. Zimmerman and Lizabeth D. Murphy, Excluded Volume Effects on the Partition of Single- and Double-Stranded Oligodeoxynucleotides Between Two Liquid Phases, Biopolymers, Oct. 1992, 1365-1373, vol. 32, Issue 10, John Wiley & Sons, Inc.

Steven B. Zimmerman and Stefan O. Trach, Excluded Volume Effects on the Partition of Macromolecules Between Two Liquid Phases, Biopolymers, 1990, 703-718, vol. 30, Issue 7-8, John Wiley & Sons, Inc.

T.Matos, et al., Isolation of PCR DNA fragments using aqueous two-phase systems, Separation and Purification Technology, Feb. 10, 2014, 144-148, vol. 122, Elsevier B.V.

Andreas Frerix, et al., Exploitation of the Coil—Globule Plasmid DNA Transition Induced by Small Changes in Temperature, pH Salt, and Poly(ethylene glycol) Compositions for Directed Partitioning in Aqueous Two-Phase Systems, Langmuir, Mar. 25, 2006, 4282-4290, vol. 22 Issue 9, American Chemical Society.

Ricky Y. T. Chiu, et al., An Aqueous Two-Phase System for the Concentration and Extraction of Proteins from the Interface for Detection Using the Lateral-Flow Immunoassay, PLOS One, Nov. 10, 2015, 1-14, PLOS, California, US.

K. Jessie, et al., Protein Precipitation Method for Salivary Proteinsand Rehydration Buffer for Two-Dimensional Electrophoresis, Biotechnology, 2008, 686-693, 7 (4), Asian Network for Scientific Information.

Richard J. Wicks, et al., The extraction and purification of DNA labelled with [methyl-3 H]thymidine in aquatic bacterial production studies, Journal of Plankton Research, 1987, 1159-1166, vol. 9 no. 6, IRL Press Limited, Oxford, England.

Donald C Rio, et al., Purification of RNA by SDS solubilization and phenol extraction. Cold Spring Harb Protoc, Jun. 2010, 1-4, vol. 2010 Issue 6, Cold Spring Harbor Laboratory Press, NY, USA.

Zsolt Czimmerer, et al., A Versatile Method to Design Stem-Loop Primer-Based Quantitative PCR Assays for Detecting Small Regulatory RNA Molecules, PLOS One, Jan. 31, 2013, 1-10, vol. 8 Issue 1, PLOS, California, US.

Wu et al., "Factors Affecting Aqueous Two-Phase Extraction", Biopharmaceutical Technology (Fourth Edition), Aug. 2015, p. 122-126, China medicine science and technology press.

"Silicone Polyethers—Silsurf", Retrieved from the internet <URL: https://www.siltech.com/products/silicone-polyethers-silsurf/#:~:text=Silicone%20polyethers%2C%20or%20silicone%20surfactants,specific%20properties%20of%20a%20product>. [retrieved on Feb. 17, 2023].

\* cited by examiner

PHASE SEPARATION BEHAVIOR MODIFYING AGENTS FOR AQUEOUS TWO-PHASE SEPARATION WITHIN POROUS MATERIAL

CROSS-REFERENCE TO RELATED APPLICATIONS

This application claims the benefit of U.S. Provisional Application No. 62/513,994, filed Jun. 1, 2017 and U.S. Provisional Application No. 62/599,001, filed Dec. 14, 2017. The entire contents and disclosures of the preceding application are incorporated by reference into this application.

Throughout this application, various publications are cited. The disclosures of these publications in their entireties are hereby incorporated by reference into this application to more fully describe the state of the art to which this invention pertains.

FIELD OF THE INVENTION

The present invention relates to a method and/or device for improving the behaviors and performance of aqueous two-phase system (ATPS) within a porous material for isolating and/or concentrating one or more target analytes from a sample solution. The present method and device are related to using one or more phase separation behavior modifying agents to improve the separation behavior and performance characteristics of ATPS components within a porous material. A modifying agent can increase the stability or reduce fluctuations of ATPS by affecting the volumes and volume ratio of the two phases after separation, fluid flow rates, and/or concentrations of the ATPS components. In one embodiment, the range of concentrations of the ATPS components for phase separation is widened significantly when a modifying agent(s) is added to the ATPS, thereby increasing the yield of a purified target analyte. The present invention further provides a device for carrying out the method of the present invention.

BACKGROUND OF THE INVENTION

The concentration of a target analyte is a critical parameter in many research and diagnostic applications. A purified target analyte must be of high quality and sufficient quantity, such that it can be used in various downstream applications including detection, clinical diagnosis and so on. Obtaining a target analyte in a purified form is a complicated task due to the presence of large amounts of cellular materials and macromolecules (e.g. proteins and carbohydrates) (also termed as 'polymers') in such samples as urine, blood, plasma, serum, saliva and other biological fluids.

For target analytes that are present at very low concentrations in biological fluids, such as urine and blood, there is a need to obtain large volumes of biological fluids in order to obtain sufficient quantity of the target analytes for subsequent detection by molecular techniques.

It has been a huge challenge to detect the existence of an analyte which has an extremely low concentration. The analyte can be a biomarker of a disease such as a cell free DNA (cfDNA), circulating tumor DNA (ctDNA) or a protein which exists in a sample such as saliva, blood, urine and other bodily fluids of a patient. Many of the existing diagnostic or detection methods may falsely report that the analyte does not exist if the analyte concentration is too low. For instance, the gold standard of diagnostics such as Polymerase Chain Reaction (PCR) and Enzyme-Linked Immune Sorbent Assay (ELISA) may produce a false negative result if the target analyte has extremely low quantity beyond the detection limit of the assay.

Despite discovery and invention of new biomarkers for many diseases in recent years, diagnostic tests based on these new biomarkers, such as cfDNA testing, have not been adopted in routine clinical procedures due to lack of sensitivity and specificity. Where biomarkers are present in low quantities, accurate detection hinges upon isolation methods that can concentrate the biomarkers from background. Depending on the isolation method, this challenge can be complicated with variance in fragment size and influences by test inhibitors.

There are methods described in the literature to concentrate target analytes. A method to concentrate an analyte by porous material dehydrated with ATPS has been disclosed in patent publication WO2017041030. However, the number of folds of concentration is rather small to satisfy the need in practice. Despite the popularity of ATPS, it is still not widely used in the industry due to its limitations. For example, it is limited by the maximum sample volume the system can process, the minimum and maximum concentration of ATPS components, and the yield of purified target analytes. Specifically, the performance of ATPS is not very stable during phase separation due to fluctuations in sample volumes, concentration and ratio of ATPS components, and so on, thereby affecting the purification of the target analytes in terms of efficiency, purity and yield.

To overcome these limitations, the present invention provides an improved method and device to concentrate and purify target analytes from samples for further analysis. Using ATPS components which are embedded within a porous material and one or more phase separation behavior modifying agents, the present methods and devices can concurrently perform a number of tasks including isolating target analytes, removing non-target analytes and impurities, and concentrating target analytes in high yield in any suitable condition, so that the methods and devices can be implemented using a wide range of concentrations of ATPS components, resulting in stable phase separation during the whole process with no or minimal fluctuations, and under different flow rates. In short, the present invention significantly improves the behaviors and performance of ATPS. The present invention further provides a device for carrying out the method of the present invention.

SUMMARY OF THE INVENTION

The foregoing background, as well as the following detailed description, are better understood when read in conjunction with the appended figures. The figures are intended to be illustrative and not limiting. The disclosure is not limited to the precise arrangements and examples shown herein.

The present invention relates to a method and/or device for improving the behaviors and performance of an aqueous two-phase system (ATPS) within a porous material for isolating or concentrating a target analyte from a sample solution. In one embodiment, the present method and/or device comprise ATPS components within a porous material, and one or more phase separation behavior modifying agents that improve the separation behavior and performance characteristics of ATPS, including but not limited to increasing the stability or reducing fluctuations of ATPS through adjustment of parameters including but not limited to the total volume of a sample solution that undergoes phase separation, volume ratio, fluid flow rates and the concentrations of ATPS components.

In one embodiment, the present method and device comprise a porous material embedded with ATPS components and one or more phase separation behavior modifying agents that widen the range of concentrations of the ATPS components effective for phase separation.

In one embodiment, the present method and device comprise a porous material embedded with ATPS components and one or more phase separation behavior modifying agents that increase the yield of purified target analytes.

In one embodiment, the present method and device comprise a porous material embedded with ATPS components and one or more phase separation behavior modifying agents that improve the stability of ATPS during phase separation by minimizing fluctuations in the volumes and/or volume ratios of the two phases.

In one embodiment, the method and device comprise a porous material embedded with ATPS components and one or more phase separation behavior modifying agents to remove contaminants from a sample solution.

In one embodiment, the present invention provides a method and/or device for concentration of a target analyte in a solution using ATPS components which are embedded in a porous material, and one or more phase separation behavior modifying agents.

In one embodiment, phase separation behavior modifying agents are compounds which can induce or promote phase separation by changing the temperature, pH, salt concentration, hydrophobicity/hydrophilicity, surface tension, and/or ionic strength of the ATPS. As a result, the target analyte partitions preferentially into one of the two phases, depending on their characteristics. In one embodiment, phase separation behavior modifying agents include compounds carrying an acidic functional group, an amine functional group, and/or both a hydrophilic group and a hydrophobic group.

In one embodiment, the present invention provides a device for isolating or concentrating one or more target analytes from a sample solution, the device comprising:
i) a porous material;
ii) components capable of forming a first phase solution and a second phase solution of an aqueous two-phase system (ATPS); and
iii) one or more phase separation behavior modifying agents; wherein said components and said phase separation behavior modifying agents are embedded in said porous material, wherein when a solution containing said target analytes flows through said porous material, an aqueous two-phase system comprising said first phase solution and said second phase solution is generated, wherein the separation behavior of the two phase solutions is altered by said phase separation behavior modifying agents, and said target analytes are isolated or concentrated on said porous material.

In one embodiment, the present invention provides a device for isolating or concentrating one or more target analytes, the device comprising:
i) a porous material;
ii) components capable of forming a first phase solution and a second phase solution of an aqueous two-phase system (ATPS); and
iii) one or more phase separation behavior modifying agents;
wherein one or more of said components and said phase separation behavior modifying agents are embedded in said porous material, wherein the balance of said components and said phase separation behavior modifying agents are to be mixed with a solution containing said target analytes, thereby forming a mixed solution, wherein when said mixed solution flows through said porous material, an aqueous two-phase system comprising said first phase solution and said second phase solution is generated, wherein the separation behavior of the two phase solutions is altered by said phase separation behavior modifying agents, and said target analytes are isolated or concentrated on said porous material.

In one embodiment, the present invention provides a method for isolating or concentrating one or more target analytes from a sample solution, the method comprising:
i) obtaining a sample solution containing the target analytes; and
ii) contacting the sample solution with a porous material embedded with one or more phase separation behavior modifying agents, components capable of forming a first phase solution and a second phase solution of an aqueous two-phase system (ATPS), wherein, when a solution containing said target analytes flows through the porous material, an aqueous two-phase system comprising said first phase solution and said second phase solution is generated,
wherein the separation behavior of the two phase solutions is altered by said modifying agents;
wherein the target analytes are isolated or concentrated on said porous material.

DETAILED DESCRIPTION OF THE INVENTION

Figure 1:
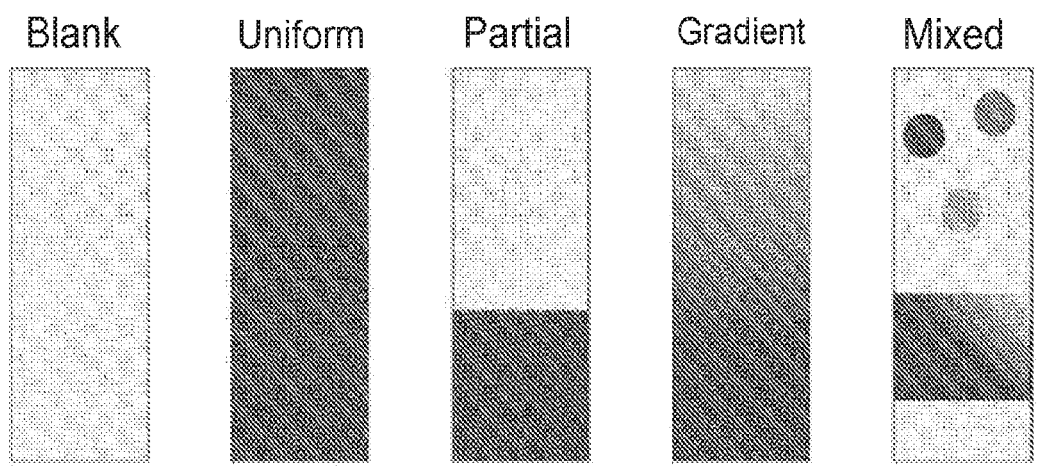
FIG. 1 provides a few embodiments showing how a phase separation behavior modifying agent can distribute within a rectangular porous material. The phase separation behavior modifying agent may be disbursed within the porous material at many different locations and at different concentrations within each location.

In the following description, several embodiments of the invention are described. For purposes of explanation, specific configurations and details are set forth in order to provide a thorough understanding of the embodiments. In addition, to the plural or singular forms of a word and to the extent that orientations of the embodiments are described as, "top", "bottom", "front", "back", "left", "right" and the like, these wordings are to aid the reader in understanding the embodiments and are not meant to be limiting physically. It is apparent to a person skilled in the art that the present invention may be practiced without specific details. The invention will be better understood by reference to the examples which follow, but those skilled in the art will readily appreciate that the specific examples are for illustrative purposes only and should not limit the scope of the invention which is defined by the claims which follow thereafter. It is to be noted that the transitional term "comprising" or "including", which is synonymous with "containing" or "characterized by", is inclusive or open-ended and does not exclude additional, unrecited elements or method steps.

The present invention relates to a method and/or device for improving the behaviors and performance of aqueous two-phase system (ATPS) within a porous material to isolate or concentrate a target analyte from a sample solution. The present invention further provides a device for carrying out the method of the present invention.

In one embodiment, among the many different possibilities contemplated, the present methods and/or devices take the advantage of the phase separation behavior modifying agents to improve one or more phase separation behaviors and performance characteristics of the ATPS components. In one embodiment, it is further contemplated that improvement in phase separation behaviors and performance characteristics of the ATPS components can improve the functionality and integration of many other devices, methods, or practices being used in conjunction with the present porous material or device.

In one embodiment, the present invention provides a method and a device for isolating or concentrating a target analyte in a solution using ATPS components which are embedded on a porous material, and one or more phase separation behavior modifying agents. In one embodiment, phase separation behavior modifying agents are compounds which can induce or promote phase separation by changing the temperature, pH, salt concentration, and/or ionic strength of the ATPS system. As a result, the target analyte partitions preferentially into one phase or the other, depending on their characteristics.

Accordingly, the present invention provides an aqueous two-phase system (ATPS) which is capable of isolating or concentrating a target analyte from a sample under a wide range of concentration of ATPS components. The present invention overcomes the limitations of the existing technologies such as limitations on sample size, minimum and maximum concentrations of ATPS components and yield of purified target analytes. The present invention facilitates a faster and efficient distribution of target analytes in the aqueous two-phase system without the need for complex instrumentation and allows purification of target analytes from large volume and complex biological materials with high yield, while avoiding target analytes contamination.

In one embodiment, the present invention provides a device for isolating or concentrating one or more target analytes from a sample solution, the device comprising:
  i) a porous material;
  ii) components capable of forming a first phase solution and a second phase solution of an aqueous two-phase system (ATPS); and
  iii) one or more phase separation behavior modifying agents;
    wherein said components and said phase separation behavior modifying agents are embedded in said porous material, wherein when a solution containing said target analytes flows through said porous material, an aqueous two-phase system comprising said first phase solution and said second phase solution is generated, wherein the separation behavior of the two phase solutions is altered by said phase separation behavior modifying agents, and said target analytes are isolated or concentrated on said porous material.

In one embodiment, the present invention provides a device for isolating or concentrating one or more target analytes, the device comprising:
  i) a porous material;
  ii) components capable of forming a first phase solution and a second phase solution of an aqueous two-phase system (ATPS); and
  iii) one or more phase separation behavior modifying agents;
  wherein one or more of said components and said phase separation behavior modifying agents are embedded in said porous material, wherein the balance of said components and said phase separation behavior modifying agents are to be mixed with a solution containing said target analytes, thereby forming a mixed solution, wherein when said mixed solution flows through said porous material, an aqueous two-phase system comprising said first phase solution and said second phase solution is generated, wherein the separation behavior of the two phase solutions is altered by said phase separation behavior modifying agents, and said target analytes are isolated or concentrated on said porous material.

In one embodiment, the present invention provides a method for isolating or concentrating one or more target analytes from a sample solution, the method comprising:
  i) obtaining a sample solution containing the target analytes; and
  ii) contacting the sample solution with a porous material embedded with one or more phase separation behavior modifying agents, components capable of forming a first phase solution and a second phase solution of an aqueous two-phase system (ATPS), wherein, when a solution containing said target analytes flows through the porous material, an aqueous two-phase system comprising said first phase solution and said second phase solution is generated, wherein the separation behavior of the two phase solutions is altered by said phase separation behavior modifying agents;
  wherein the target analytes are isolated or concentrated on said porous material.

In one embodiment, when ATPS is applied on a porous material (e.g. paper), the two phases of the ATPS separate from each other as the mixed phase solution flows through the porous materials. The resulting phase solutions are of different physicochemical properties and each phase travels through the porous matrix at different rates. Different molecules in a mixture would be distributed differentially between the two phase solutions due to their different properties, and it is possible to separate and concentrate target molecules using ATPS with minimal set up and human intervention.

The advantage of the invention is that high concentration and high yield of the target analyte can be obtained in a simple way and compatible with downstream application analysis without further step of purification or concentration.

The methods and devices provided herein are robust, inexpensive, simple, easy to handle, safe, user friendly and fast. The present method and device are able to purify and concentrate the target analyte and thereby ensure the performance of the downstream applications using the purified and concentrated analyte will not be affected by impurities in the original sample.

Furthermore, the present invention is applicable to samples containing the target analyte in a very low amount, or of a small volume and is readily adaptable to automation including high throughput screening systems.

In one embodiment, the present invention provides a method and/or device comprising ATPS as a concentration module linked with a lateral flow immunoassay (LFA) component as a detection module. In one embodiment, the detection module is housed in a plastic housing with a viewing window and gold nanoprobes. As the sample wicks up the device and ATPS components undergo phase separation, the analytes are concentrated substantially in the leading front. Concentrated analytes are then detected by the LFA module generating visual test results.

Type of Samples and Target Analytes

In one embodiment, the present method and device can separate a target analyte from non-target molecules (e.g., small molecules and macromolecules which are typically of natural origin and may interfere with the detection or quantification of target analyte) in a sample and thereby allows a more accurate detection and diagnosis.

In one embodiment, the present method and device are applicable to any types of sample. In one embodiment, samples include but are not limited to food, blood, plasma, serum, tissues, bacteria, viruses, RNA viruses, smear preparations, bacteria cultures, cell cultures (e.g. cell suspensions and adherent cells), urine, saliva, fecal matters, and bodily discharges (e.g. tears, sputum, nasopharyngeal mucus, vaginal discharge and penile discharge), polymerase chain reaction (PCR) mixtures and in vitro nucleic acid modification reaction mixtures.

In one embodiment, the target analytes include but are not limited to proteins, nucleic acids, carbohydrates, lipids, bacteria, virus, pathogens, food allergen and nanoparticles and the like.

In one embodiment, the target analyte is a food allergen including but is not limited to vegetable protein and animal protein. Lupine protein is more prefer in the invention.

In one embodiment, the target analyte is a nucleic acid of various types (e.g. DNA including cDNA, RNA including mRNA and rRNA), forms (e.g. single-stranded, double-stranded, coiled, as a plasmid, non-coding or coding) and lengths (e.g. an oligonucleotide, a gene, a chromosome and genomic DNA), originated from the subject or an exogenous agent or both.

In one embodiment, the target analyte is a protein which is a peptide or a polypeptide, including an intact protein molecule, a degraded protein molecule and digested fragments of a protein molecule. In one embodiment, biomarkers include but are not limited to antigens, receptors and antibodies, originated from the subject or an exogenous agent or both.

In one embodiment, the target analyte is a small molecule such as a metabolite. In one embodiment, the metabolite is a disease-related metabolite which is indicative of the presence or extent of a disease or a health condition. In one embodiment, the metabolite is a drug-related metabolite such as a drug by-product of which the level changes in a subject body consuming the drug.

In one embodiment, the target analyte is originated from the subject himself or herself (e.g. molecules that are derived or released from any organs, tissues or cells of the subject), an exogenous source (e.g. a pathogen such as virus or bacteria associated with a particular disease), or a food allergen (protein) from food or drug taken by the subject. *S. mutans* is the prefer bacteria in this invention.

In one embodiment, the target analyte is not normally found in healthy subject. In one embodiment, the target analyte is a molecule that is normally found in a healthy subject but the level of which is indicative of a particular disease or a health condition.

ATPS (Aqueous Two-Phase System) within Porous Material

In one embodiment, the present invention provides use of ATPS components within a porous material. Various ATPS systems can be used in the present invention, including but are not limited to polymer-polymer (e.g. PEG-PVP), polymer-salt (e.g. PEG-salt), and micellar. Porous material may be made of any suitable porous material which can absorb and transfer liquid. Suitable porous materials for this invention include but are not limited to hydrogel, fiberglass paper, cotton-based paper, other types of paper, polymer foams, cellulose foams, other types of foams, rayon fabric, cotton fabric, other types of fabric, wood, stones, and any other materials that can absorb and transfer liquid.

In one embodiment, the present invention provides uses of ATPS (aqueous two phase system) for the isolation and/or concentration of a target analytes in a sample solution, wherein the phase separation characteristics are altered by one or more phase separation modifying agents that improve the behaviors and performance of the ATPS, thereby induces or promotes phase separation of the ATPS.

In one embodiment, the ATPS comprises a mixed phase solution comprising a first phase solution and a second phase solution, wherein components of said first phase solution and components of said second phase solution are embedded in said porous material at a concentration or a loading that is sufficient to undergo a phase separation as the mixed phase solution flows through the porous material. In one embodiment, the phase separation characteristics are altered by one or more phase separation modifying agents so as to induce, stabilize and/or promote phase separation of the ATPS.

In one embodiment, components of the first phase solution and/or the components of said second phase solution of the ATPS are embedded in the porous material and then dehydrated prior to the addition of a sample containing the target analyte to said porous material.

In one embodiment, components of the first phase solutions and/or the components of said second phase solution of the ATPS are combined with a sample containing the target analyte to create a mixture prior to the addition of said mixture to the porous material.

In one embodiment, some of the components of the first phase solution and/or the components of the second phase solution of the ATPS are embedded in the porous material and then dehydrated, while the remaining components of the first phase solutions and/or the components of the second phase solution are combined with a sample containing the target analyte to create a mixture prior to the addition of the mixture to the porous material.

In one embodiment, there is provided a two-component ATPS (aqueous two phase system) within a porous material for the concentration of one or more target analytes and/or the purification of a sample solution. The target analyte is in contact with the mixed phase solution comprising a first phase solution and a second phase solution, and partitions into the first phase solution, the second phase solution or the interface (or interphase) between the first phase solution and the second phase solution.

In one embodiment, there is provided a two-component ATPS (aqueous two-phase system) within a porous material for removing one or more contaminants from a sample, thereby obtains a purified sample of the target analyte(s). In one embodiment, the one or more contaminants are in contact with the mixed phase solution comprising a first phase solution and a second phase solution, and wherein the contaminants partitions into the first phase solution, the second phase solution, or the interface (or interphase) between the first phase solution and the second phase solution.

In one embodiment, the porous material and ATPS are selected so that the first phase solution flows through the porous matrix at a first rate and the second phase solution flows through the porous matrix at a second rate, wherein the first rate and the second rate are different.

In one embodiment, the porous material is commercially available or manufactured in-house.

Phase Separation Behavior Modifying Agents

In one embodiment, the present method and device comprise a porous material embedded with ATPS components and one or more phase separation behavior modifying agents that modify the phase separation behavior of the ATPS and thereby inducing or promoting phase separation. In one embodiment, the present phase separation behavior modifying agents are capable of widening the range of concentrations of ATPS components that are effective for phase separation.

In one embodiment as shown in FIG. 1, it is further contemplated that the present method and device may use different types of phase separation behavior modifying agents at various combinations. In one embodiment, it is further contemplated that the phase separation behavior modifying agent(s) can be disbursed within the porous material of the device at many different locations and at different concentrations within each location.

A binodal curve denotes the conditions (e.g. temperature and concentrations of the phase components) at which two distinct phases may coexist and hence shows the boundary of conditions under which phase separation will occur. Under the theory of binodal curve, any point outside the binodal curve represents a monophasic system (no phase separation), while any point inside the binodal curve represents a diphasic system (phase separation).

Figure 2:
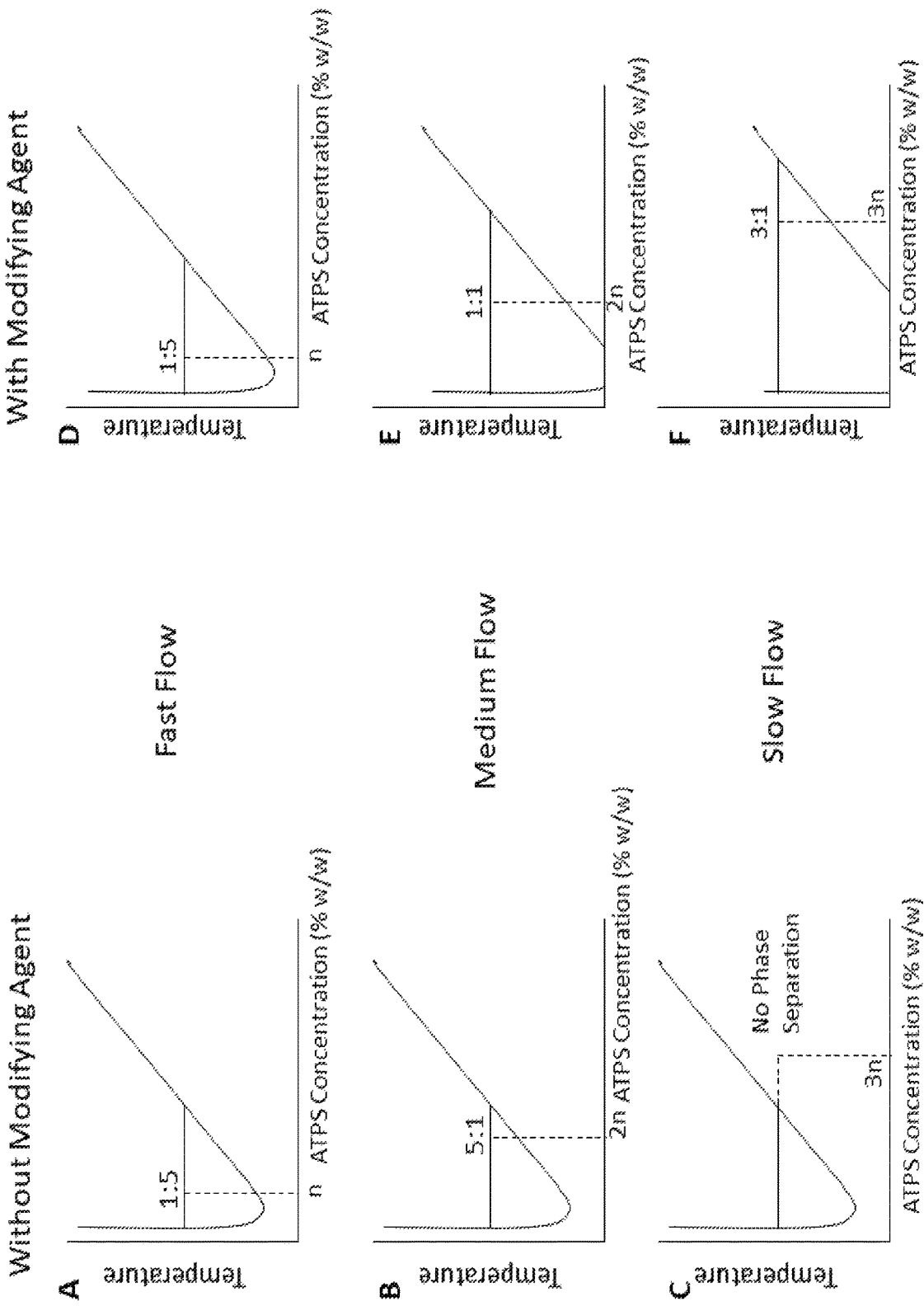
FIG. 2 shows phase separation diagrams (binodal curves) under various flow rates comparing the separation behavior and characteristics of ATPS components with or without behavior modifying agents, illustrating benefits of phase separation behavior modifying agents on phase separation characteristics of the ATPS components. In some instances, these phase separation diagrams represent a time progression of fluid flowing through a porous material embedded with ATPS components and thereby resolubilizing ATPS components that are dehydrated in that material. As time goes on, more ATPS components will get into solution. The curved lines are binodal curves which indicate the relative concentrations of ATPS components that are effective for phase separation, thereby setting a boundary between a monophasic system and a diphasic system. Under the theory of binodal curve, phase separation occurs only when the relative concentration of the ATPS components has reached a certain value. Any point outside the binodal curve represents a monophasic system (no phase separation), while any point inside the binodal curve represents a diphasic system (phase separation). The horizontal solid line refers to a tie line which denotes conditions under which the two phases exist in equilibrium with each other at a particular temperature. All systems on the tie line produce the same two phases at a given temperature and the intersections of the tie line with the binodal curve represent the compositions of the two phases that exist in equilibrium with each other at that temperature. The volume ratio of the ATPS solution can be determined by comparing the length of the point on the tie line to the binodal curve on the left to the length of the point to the binodal curve on the right (referred to as the "lever arm rule"). For example, in Panel A of FIG. 2, the volume ratio of the two phase solutions is 1:5 when the relative concentration of ATPS components is n, while in Panel B of FIG. 2 the volume ratio is 5:1 when the relative concentration of ATPS components is 2n. In contrast, when the relative concentration of ATPS components is 3n falling outside the tie line, the two phase solutions will not undergo a phase separation and remain as one single phase (Panel C of FIG. 2). Accordingly, the partition coefficient of a target analyte is the same along the tie line regardless of changes in the relative concentration of ATPS components. Since the yield of the target analyte by ATPS depends on the partition coefficient of the target analyte and the volume of the target phase recovered, the yield will depend on the tie line and the position of the ATPS on that tie line. Typically, the longer the tie line is, the higher the yield will be. The phase diagrams on the right panel (Panels D-F of FIG. 2) indicated that addition of phase separation behavior modifying agent to the ATPS shifts the position of the binodal curve downward and thus increases the length of the tie line at any given temperature, thereby allowing phase separation to occur within a wider range of relative concentration of the two phase components, as well as increasing the partition coefficient. As a result, the range of ATPS concentration capable of phase separation is widened significantly. Furthermore, in certain embodiments where the ATPS components and the phase separation behavior modifying agents are dehydrated within the porous material, the phase separation volume ratio becomes more stable with respect to flow rate and fluctuations in the concentration of the ATPS components. Along the same tie line, an increase in ATPS component concentration will result in more extreme volume ratios. Under the theory of binodal curve, if the operating relative concentration of ATPS components is too close to either side of the binodal curve, even a slight change of volume ratio of the two phase solutions (e.g. a slight dilution or concentration of the solutions) can cause a shift of the operating relative concentration to another side of the binodal curve where only one phase exists. However, in cases where the porous material is embedded with both the ATPS components and modifying agents in dehydrated form, the increase in ATPS component concentration also correlates with an increase in phase separation behavior modifying agents, and therefore leading to a proportional downward shift of the binodal curve and a longer tie line at temperature T as compared to the phase diagrams in Panels A-C of FIG. 2. As such, the same relative concentration of ATPS components would have a smaller influence on the volume ratio when modifying agents are present, making the system more stable and robust. It should be noted that FIG. 2 is illustrative of a temperature dependent ATPS with a single ATPS component, however the concept described above similarly applies to ATPSs that are not temperature dependent and ATPSs that have multiple ATPS components.

FIG. 2 shows phase separation diagrams (binodal curves in terms of temperature and relative concentrations of components forming the first and second phase of the ATPS) under various flow rates comparing the separation behavior and characteristics of ATPS components with or without adding behavior modifying agent to the system. On the left panel where no phase separation behavior modifying agent is added to the ATPS (Panels A-C of FIG. 2), two points can be observed on the binodal curve at a given temperature (except the extremum of the binodal curve), denoting a range of relative concentrations of the two-phase components at which the solution will undergo a phase separation at that temperature. A solution of a certain composition having a relative concentration outside the range will exist as one single phase. On the right panel where phase separation behavior modifying agent is added to the ATPS (Panels D-F of FIG. 2), similarly two points can be observed on the binodal curve at a given temperature and concentration of the modifying agent (except the extremum of a binodal curve). In FIG. 2, the horizontal solid line ("tie line") within the boundary of the binodal curve denotes conditions under which the two phases exist in equilibrium with each other at a given temperature. All systems on a particular tie line produce the same two phases at that given temperature and the intersections of the tie line with the binodal curve represent compositions of the two phases that exist in equilibrium with each other at that temperature. The volume ratio of the ATPS solution can be determined by comparing the length of the point on the tie line to the binodal curve on the left to the length of the point to the binodal curve on the right (referred to as the "lever arm rule"). For example, in Panel A of FIG. 2, the volume ratio of the two phase solutions is 1:5 when the relative concentration of ATPS components is n, while in Panel B of FIG. 2 the volume ratio is 5:1 when the relative concentration of ATPS components is 2n. In contrast, when the relative concentration of ATPS components is 3n falling outside the tie line, the two phase solutions will not undergo a phase separation and remain as one single phase (Panel C of FIG. 2). Accordingly, the partition coefficient of a target analyte is the same along the tie line regardless of changes in the relative concentration of ATPS components. Since the yield of the target analyte recovered by ATPS depends on the partition coefficient of the target analyte and the volume of the target phase recovered, the yield will depend on the tie line and the position of the ATPS on that tie line. Typically, the longer the tie line is, the higher the yield will be. The phase diagrams on the right panel (Panels D-F of FIG. 2) indicated that addition of phase separation behavior modifying agent to the ATPS shifts the position of the binodal curve downward and thus lengthening the tie line at any given temperature, thereby allowing phase separation to occur within a wider range of relative concentration of the two phase components, as well as increasing the partition coefficient. The range encompassed by the two points on the binodal curve is always wider in the presence of modifying agents regardless of the flow rate. Furthermore, in certain embodiments where the ATPS components and the phase separation behavior modifying agents are dehydrated within the porous material, the phase separation volume ratio becomes more stable with respect to flow rate and fluctuations in the concentration of the ATPS components. Along the same tie line, an increase in ATPS component concentration will result in more extreme volume ratios. Under the theory of binodal curve, if the operating relative concentration of ATPS components is too close to either side of the binodal curve, even a slight change of volume ratio of the two phase solutions (e.g. a slight dilution or concentration of the solutions) can cause a shift of the operating relative concentration to another side of the binodal curve where only one phase exists. However, in cases where the porous material is embedded with both the ATPS components and modifying agents in dehydrated form, the increase in ATPS component concentration also correlates with an increase in phase separation behavior modifying agents, and therefore leading to a proportional downward shift of the binodal curve and a longer tie line at temperature T as compared to the phase diagrams in Panels A-C of FIG. 2. As such, the same relative concentration of ATPS components would have a smaller influence on the volume ratio when modifying agents are present, making the system more stable and robust. It should be noted that FIG. 2 is illustrative of a temperature dependent ATPS with a single ATPS component, however the concept described above similarly applies to ATPSs that are not temperature dependent and ATPSs that have multiple ATPS components.

The binodal curves theory displayed in FIG. 2 is generally applicable to all type of modifying agents, including modifying agents described herein. It is believed that the phase separation behavior modifying agents are capable of altering the characteristics such as temperature, pH, hydrophobicity/hydrophilicity, surface tension, and/or ionic strength of one of the phase components or both and allowing phase separation to occur within a wider range of relative concentration of the two-phase components, thereby triggering or promoting phase separation of ATPS.

In one embodiment, addition of phase separation behavior modifying agents to ATPS components within a porous material improves the separation behavior and performance characteristics of the ATPS components, including but not limited to increasing the stability or reducing fluctuations of ATPS through adjustment of parameters including but are not limited to total volume of a sample solution that undergoes phase separation, volume ratio, fluid flow rates and concentration of ATPS components.

In one embodiment, the present method and device comprise a porous material embedded with ATPS components and one or more phase separation behavior modifying agents to increase the yield of purified target analytes.

In one embodiment, the present method and device comprise a porous material embedded with ATPS components and one or more phase separation behavior modifying agents that improve the stability of ATPS during phase separation by minimizing fluctuations in the ATPS.

In one embodiment, the method and device comprise a porous material embedded with ATPS components and one or more phase separation behavior modifying agents to remove contaminants from a sample solution.

In one embodiment, the phase separation behavior modifying agent(s) is/are combined with a sample containing the target analyte, and/or one or more ATPS components to create a mixture prior to the addition of said mixture to the porous material. In one embodiment, the phase separation behavior modifying agent(s) is/are combined with a sample containing the target analyte, and/or one or more ATPS components in a sequential order prior to the addition of each to the porous material.

In one embodiment, the phase separation behavior modifying agent(s) is/are embedded in the porous material containing ATPS components and then dehydrated prior to the addition of a sample to the porous material.

In one embodiment, some of the phase separation behavior modifying agent(s) is/are embedded in the porous material containing ATPS components and then dehydrated, while the remaining phase separation behavior modifying agent(s) is/are combined with a sample containing the target analyte to create a mixture prior to the addition of the mixture to the porous material.

In one embodiment, some of the phase separation behavior modifying agent(s) is/are embedded in the porous material containing components of either the first or second phase solution of the ATPS and then dehydrated, while the remaining phase separation behavior modifying agent(s) is/are combined with components of the other phase solution of the ATPS to create a mixture prior to the addition of said mixture to the porous material.

In one embodiment, some of the phase separation behavior modifying agent(s) is/are embedded on the porous material without ATPS components and then dehydrated, while the remaining phase separation behavior modifying agent(s) is/are combined with components of the first phase solution of the ATPS and components of the second phase solution of the ATPS to create a mixture prior to the addition of said mixture to the porous material.

In one embodiment, the phase separation behavior modifying agent(s) is/are present in a dry form in some regions of the porous material. In one embodiment, the phase separation behavior modifying agent(s) is/are embedded in some regions of the porous material. In another embodiment, the phase separation behavior modifying agent(s) is/are embedded in the entire region of the porous material.

In one embodiment, the phase separation behavior modifying agent(s) is/are present in a dry form at a uniform concentration across all the regions of the porous material. In another embodiment, the phase separation behavior modifying agent(s) is/are present in a dry form at varying concentrations in different regions of the porous material.

In one embodiment, the present separation behavior modifying agents include but are not limited to:
 a. compounds carrying an acidic functional group in aqueous solution, selected from dextran, sucrose, saccharides, polysaccharides, sorbates, polysorbates, carboxylates, polycarboxylates, phosphates, potassium phosphate, polyphosphates, sulfates and polysulfates, polyols;
 b. compounds carrying an amine functional group in aqueous solution, selected from amines, polyamines, amine salts and polyamine salts;
 c. compounds carrying both a hydrophilic group and a hydrophobic group, selected from lipids, surfactants, nucleic acids, hormones, proteins, amino acids;
 d. chaotropic agents; and
 e. kosmotropic agents.

In one embodiment, the present phase separation behavior modifying agents include, but are not limited to, sucrose, potassium phosphates, dextran, Tween-20 and Triton-X114.

Adjusting or Stabilizing the Total Volume of Either Phase or Both Phases

In one embodiment, the present phase separation behavior modifying agent(s) is/are selected to:
 a) reduce fluctuations (increase stability) in the total volume of either or both phases during and after phase separation. For example, when the ATPS components are embedded and dehydrated within a porous material and resolubilized during fluid flow, continued resolubilization of the ATPS components will change the total volumes of the first phase and/or the second phase. Variability in flow rates results in variability in the total volumes of the first phase and/or the second phase. In one embodiment, a modifying agent such as compound carrying both hydrophilic and hydrophobic group is used, the compound interacts with the dehydrated ATPS components within the porous material and hence reduce the fluctuations of total volume of the first phase and/or the second phase during the flow of fluid within the porous material. Reduced fluctuations in the fold of concentration is desirable for more robust devices; or
 b) increase the total volume of a sample solution that undergoes phase separation. When the ATPS components are dehydrated within a porous material and resolubilized during fluid flow, continued resolubilization of the ATPS components will increase the total volume of the first phase and/or the second phase. In one embodiment, a compound carrying acidic functional group in aqueous solution is used as a modifying agent to decrease the pH value of the first phase and/or the second phase solution and thereby promoting resolubilization of the first phase and/or the second phase solution and increasing the total volume of the phase solution. Overall, the compound carrying acidic function group will cause phase separation to occur earlier and/or at a lower concentration of ATPS within a porous material, this will result in a larger volume of the fluid undergoing phase separation as it flows through the porous material. This may be beneficial to concentrate more target from a given solution in the phase of interest; or
 c) decrease the total volume of a sample solution that undergoes phase separation. In one embodiment, a compound carrying amine functional group in aqueous solution is used as a modifying agent to increase the pH value of the first phase and the second phase and thereby hindering the resolubilization of the two phases. When the ATPS components are dehydrated within a porous material and resolubilized during fluid flow, the hindered resolubilization of the ATPS components will decrease the total volume of the first phase and/or the second phase. Therefore, phase will separate later and/or at a higher concentration of ATPS components within a porous material, this will decrease the total volume of the fluid undergoing phase separation as it flows through the material. This may be beneficial to concentrate more target from a given solution in the phase of interest.

Adjusting or Stabilizing the Volume Ratio of the First and the Second Phase

In one embodiment, the present phase separation behavior modifying agent(s) is/are selected to:
 a) reduce fluctuations (increase stability) in the volume ratio between the first and the second phase of the ATPS during or after the course of phase separation. When the ATPS components are dehydrated within a porous material and resolubilized when the fluid flows within the porous material, continued resolubilization of the ATPS components will change the volume ratio of the two phases. Variability in flow rates results in variability in volume ratio. In one embodiment, by adding a modifying agent such as compound carrying both hydrophilic and hydrophobic groups, the agent will interact with the dehydrated ATPS components by hydrophilic and hydrophobic groups and reduce the fluctuations in the volume ratio when the fluid flows within the porous material. Reduced fluctuations in volume ratio is desirable for more robust devices; or
 b) increase the volume ratio between the first and the second phase of the ATPS. In one embodiment, by adding a modifying agent such as compound carrying acidic functional group in aqueous solution to an ATPS (depending on which phase is the phase of interest), the pH value in the phase of interest will be decreased and thereby promoting the resolubilization of that phase of interest. An increase in volume ratio may be useful to further increase target concentration, to improve the flow of fluid, or to desirably adjust the volume of the phase of interest. This may be beneficial to concentrate more target from a given solution in the phase of interest; or
 c) decrease the volume ratio between the first and the second phase of the ATPS. In one embodiment, by adding a modifying agent such as a compound carrying amine functional group in aqueous solution to an ATPS (depending on which phase is the phase of interest), the pH value in the phase of interest will be increased and thereby hindering the resolubilization of that phase of interest. A decrease in volume ratio may be useful to further increase target concentration, to improve the flow of fluid, or to desirably adjust the volume of the fluid phase of interest. This may be beneficial to concentrate more target from a given solution in the phase of interest.

Adjusting the Concentrations of the First and the Second Phase Components

In one embodiment, the present phase separation behavior modifying agent(s) is/are selected to:
a) reduce fluctuations in the concentrations of the first phase component and/or the second phase component within the first phase or within the second phase. When the ATPS components are embedded on and dehydrated within a porous material and resolubilized during fluid flow, continued resolubilization of the ATPS component will change the concentrations of the first phase components and/or the second phase components. Variability in flow rates results in variability in the concentrations of components in the first phase and/or second phase. In one embodiment, by adding a modifying agent such as a chemical carrying both hydrophilic and hydrophobic groups into the solution or the porous material, the agent will interact with ATPS components by hydrophilic and hydrophobic groups and reduce the fluctuations in the concentration when the fluid flows within the porous material. Reduced fluctuations in the fold of concentration is desirable for more robust devices; or
b) increase the concentration of components of one phase of the ATPS within the same phase. In one embodiment, when the ATPS components are dehydrated within the porous material, by either adding a modifying agent such as a chemical carrying acidic functional group in aqueous solution directly to the solution containing the target analyte or dehydrating the modifying agent within the porous material, the pH value in that phase solution will be will decreased and thereby promoting resolubilization of the ATPS components in that phase, resulting in a higher concentration. This may be beneficial to increase the concentration factor and thus enhance the concentration of the target analyte by increasing the volume ratio which causes more volume to undergo phase separation. This may be beneficial to concentrate more target from a given solution in the phase of interest; or
c) decrease the concentration of components of one phase of the ATPS within the same phase. In one embodiment, by either adding a modifying agent such as a compound carrying amine functional group in aqueous solution directly to the solution containing the target analyte or dehydrating the modifying agent within the porous material, it will increase the pH value and reduce the rate of resolubilization of ATPS components of that phase, thus resulting in a lower concentration of ATPS components of one phase within the same phase during resolubilization. This may be beneficial to create a more sustained release of ATPS components as the fluid flows within the porous material, resulting in a more uniform ATPS concentration and a larger volume that undergoes phase separation. This may be beneficial to concentrate more target from a given solution in the phase of interest; or
d) increase the concentration of the components of one phase within the other phase. In one embodiment, when the ATPS components are dehydrated within the porous material, by either adding a compound carrying acidic functional group in aqueous solution directly to the solution containing the target analyte or dehydrating the modifying agent within the porous material, the pH value of the first phase components within the second phase will be decreased and thereby promoting resolubilization of components of the first phase within the second phase solution, resulting in a higher concentration of the first phase components within the second phase. This may be beneficial to increase the volume ratio, cause more volume to undergo phase separation, and/or increase the concentration of the target analyte. This may be beneficial to concentrate more target from a given solution in the phase of interest; or
e) decrease the concentration of components of one phase of the ATPS within the other phase. In one embodiment, by either adding a modifying agent such as a compound carrying amine functional group in aqueous solution directly to the solution containing the target analyte or dehydrating the modifying agent within the porous material, the pH value and the rate of resolubilization of components of that phase will be increased, thus resulting in a lower concentration of ATPS components of one phase within the other phase during resolubilization. This may be beneficial to create a more sustained release of ATPS component as the fluid flows within the porous material, resulting in more uniform ATPS concentration and a larger volume that undergoes phase separation. This may be beneficial to concentrate more target from a given solution in the phase of interest; or
f) any combination of a-e.

Inducing Phase Separation at an Earlier Time and/or at a Lower Concentration of ATPS Components Within a Porous Material In one embodiment, by causing the phase separation to occur earlier and/or at a lower concentration of ATPS components within a porous material, this will result in a larger volume of the fluid undergoing phase separation as it flows through the porous material. In one embodiment, this can be achieved by adding a modifying agent such as a compound carrying acidic functional group in aqueous solution to decrease the pH value of the first and/or second phase and thereby promoting the resolubilization of the phase components. When the ATPS components are dehydrated within a porous material and resolubilized as the fluid flows, continued resolubilization of the ATPS components will increase the total volumes of the first phase and/or the second phase. This may be beneficial to concentrate more target from a given solution. In one embodiment, the phase separation behavior modifying agent(s) is/are selected to induce initial phase separation at a lower concentration of the ATPS components that would otherwise be too low to induce phase separation in the absence of said phase separation behavior modifying agent(s). In one embodiment where the ATPS comprises a micellar solution, when the concentration of ATPS components is insufficient to cause a phase separation, one or more modifying agents can be added to alter parameters of the ATPS components such as temperature, pH value or ionic strength to allow phase separation at a lower concentration. This would benefit situations where the temperature is too low to run the diagnostic, i.e., by expanding the operating temperature range, or situations where a downstream diagnostic component was sensitive to the ATPS components which requires their concentrations be kept at low level.

In one embodiment, by causing the phase separation to occur earlier and/or at a lower concentration of ATPS components within a porous material, it will result in a larger volume of the fluid undergoing phase separation as it flows through the porous material. In one embodiment, this can be achieved by adding a modifying agent such as a compound carrying acidic functional group in aqueous solution to decrease the pH value of the first phase and/or second phase and thereby promoting the resolubilization of the components. When the ATPS components and/or modifying agents are dehydrated within a porous material and resolubilized as the fluid flows, continued resolubilization of the ATPS component will increase the total volume of the first phase and/or the second phase. This may be beneficial to concentrate more target analyte from a given solution. In situations where the ATPS components are dehydrated within the porous material and require resolubilization, phase separation will only occur once the concentration has reached a certain point. By adding a modifying agent that induces phase separation at a lower concentration of the ATPS components, phase separation will start earlier at a more upstream position within the porous material. This may be beneficial to increase the total volume that undergoes phase separation and thus concentrate more target analyte for the downstream application.

In one embodiment as shown in FIG. 1, the present method and/or device may use many different types and many variations of combinations of phase separation behavior modifying agents. In one embodiment, the phase separation behavior modifying agent(s) may be distributed within the porous material of the device at multiple different locations and/or at different concentrations within each location.

Adjusting the Rate of Domain Coalescence of the ATPS

Domain coalescence is the process where small drops of one phase of an ATPS coalescing together to form a larger volume of that phase. In one embodiment, the present phase separation behavior modifying agent(s) is/are selected to:
 a) reduce fluctuations in the rate of domain coalescence of one or both phases of an ATPS. In one embodiment, by adding charged surfactant or protein that are self-interacting to the solution, these agents will partition to the interface between the domains of one of the phases and increase domain to domain interaction, thereby reducing the fluctuations in the rate of domain coalescence; or
 b) increase the rate of domain coalescence of one or both phases of an ATPS. In one embodiment, by adding charged surfactant or protein that are self-interacting to the solution, these agents will partition to the interface between the domains of one of the phases and increase domain to domain interaction, thus increasing the rate of domain coalescence. This may be beneficial to speed up the run time of the diagnostic; or
 c) decrease the rate of domain coalescence of one or both phases of an ATPS. In one embodiment, by adding surfactant to the solution which decreases the surface tension between the two phases. With decreased surface tension, there is less of a thermodynamic force to drive domain coalescence. This may be beneficial in situations where the target analyte partition slowly and hence requires more time to get to the appropriate phase which is facilitated by keeping domain small initially by slowing down their coalescence;

Adjusting the Flow Rate of Fluids

In one embodiment, the flow rate within a porous material can be increased or decreased by adding agents that change the viscosity and/or hydrophobicity of the solution. Generally, flow rate of fluid is inversely proportional to its viscosity. Flow rate also increases as the hydrophobicity of the fluid becomes more similar to the porous material. In one embodiment, the present phase separation behavior modifying agent(s) is/are selected to:
 a) reduce fluctuations in the flow rate within the porous matrix of the first phase, or the second phase. In one embodiment, by adding a modifying agent such as compound carrying both hydrophilic and hydrophobic groups, the agent will interact with ATPS components by hydrophilic and hydrophobic groups and reduce the fluctuations in flow rate; or
 b) increase the flow rate within the porous matrix of the first phase or the second phase. In one embodiment, by adding a modifying agent such as a compound carrying hydrophilic groups, the agent will interact with ATPS components by hydrophilic groups to decrease the ionic strength of the system and as a result, decrease the viscosity and hydrophobicity of the solution and the flow rate will increase; or
 c) decrease the flow rate within the porous matrix of the first phase or the second phase. In one embodiment, by adding a modifying agent, such as a compound carrying hydrophobic groups, the agent will interact with ATPS components by hydrophobic groups to increase the ionic strength of the system. As a result, the viscosity and hydrophobicity of the solution are increased and the flow rate will decrease; or
 d) any combination of a-c.

Adjusting the Partitions of Target Analyte or Contaminants into the First or Second Phase Components In one embodiment, the present phase separation behavior modifying agent(s) is/are selected to:
 a) reduce fluctuations in the partitioning of target analyte and/or contaminants between the first phase and the second phase; or
 b) increase the partition of the target analyte and/or contaminants to the phase of interest. Target partitioning can be driven by a variety of forces/principles including without limitation size exclusion principles, hydrophobic/hydrophilic interactions, electrostatic interactions. In one embodiment, by adding modifying agent that changes the environment within a phase, partitioning of the target analyte to the phase of interest can be increased. For example, the addition of chaotropic agents will make the hydrophobic phase more hydrophobic by disrupting the hydrogen bonds in the interested phase, thus increasing the partitioning of hydrophobic analyte or contaminants to that phase. This may be beneficial to further increase concentration of the target analyte or contaminants; or
 c) decrease the partition of the target analyte and/or contaminants to the phase of interest. In one embodiment, adding kosmotropic agents will make the hydrophobic phase more hydrophilic by increasing the interactions between the two phases, thus decreasing the partitioning of hydrophobic analyte or contaminants to that phase. This may be desirable if one is trying to separate two targets into different phases; or
 d) any combination of a-c.

In one embodiment, the phase separation behavior modifying agent(s) is/are selected to perform any combination of functions described above.

Adjustment of Concentration Factors

In one embodiment, the relative amounts of ATPS components in the porous material can be changed.

In one embodiment, by changing the amounts of ATPS components dehydrated on the porous material and thereby the volume ratio of the two phases, the target analyte can be preferentially concentrated in one phase. In one embodiment, the target analyte is retained in the leading front of the ATPS, which is then collected and optionally further analyzed using appropriate technologies.

In one embodiment, the order of ATPS components on the porous material can be adjusted to achieve the desired effect or phenomenon. In one embodiment, one or more ATPS components can be dehydrated and embedded in the porous material.

In one embodiment, to better quantify the phenomena associated with the present invention, an assay was developed to evaluate the correlation between the relative amounts of ATPS components dehydrated on the porous material and the fold of concentration achieved. In one embodiment, the concentration factor can be controlled and fine-tuned by adjusting the relative amount of the ATPS components as needed.

In one embodiment, to integrate the ATPS components into the porous material, the ATPS components were solubilized in water (or appropriate buffer) and applied a predetermined amount of the solution/suspension on the porous material. The porous materials were then placed in a lyophilizer or equivalent solvent-removing equipment to remove solvent (e.g., water), resulting in dehydration of the ATPS components directly on the porous material. Upon introduction of the sample solution to the porous material, the ATPS components instantly undergo rehydration and thereby separating the components or molecules in the sample as they flow within the porous material and concentrating the target analyte at the front of the fluid flow. In one embodiment, no external power or equipment is required to provide a driving force.

In one embodiment, the present invention provides a device comprising a porous fiberglass paper that is impregnated with a polymer/polymer ATPS, e.g., PEG-PVP ATPS. When a sample containing a plurality of analytes is applied to one end of the device, the impregnated porous fiberglass paper causes the analyte-containing ATPS component to preferentially flow ahead of the other ATPS components. Therefore, the target analyte is concentrated in the analyte-containing ATPS component at the front of the fluid flow.

In one embodiment, the present invention provides a device comprising a porous fiberglass paper that is pretreated with a polymer-salt ATPS, e.g., PEG-salt ATPS. When a sample containing a plurality of analytes is applied to one end of the device, the pretreated porous fiberglass paper causes the analyte-containing ATPS component to preferentially flow ahead of the other ATPS components. Therefore, the target analyte is concentrated in the analyte-containing ATPS component at the front of the fluid flow.

In one embodiment, the present invention provides a device comprising a porous fiberglass paper is impregnated with a micellar ATPS. When a sample containing a plurality of analytes is applied to one end of the device, the impregnated porous fiberglass paper causes the analyte-containing ATPS component to preferentially flow ahead of the other ATPS component. Therefore, the target analyte is concentrated in the analyte-containing ATPS component at the front of the fluid flow.

In one embodiment, the sample solution suitable for the device/method disclosed in the present invention is a buffer solution, which includes, but is not limited to, phosphate-buffered saline (PBS), and Tris-EDTA (TE) buffer. In this invention, preferably, the buffer solution is PBS buffer (8 mM Sodium chloride, 0.2 mM Potassium chloride, 1.15 mM Sodium monohydrogen phosphate, 0.2 mM Potassium dihydrogen phosphate solution with pH 7.35-7.65). In one embodiment, the buffer solution is TE buffer containing 2% bovine serum albumin (BSA), 0.1% PEG and 20 mM Tris, pH 7.5 respectively.

In one embodiment, multiple ATPS components are incorporated into a porous material to achieve a control of concentration factors of the target analyte.

In one embodiment, the optimized ratios of the ATPS components are implemented in a polymer/salt ATPS, polymer/polymer ATPS, or micellar ATPS to control the concentration factors.

In one embodiment, the ratios of the ATPS components are adjusted to demonstrate concentration factors between 10 folds and 100 folds.

In one embodiment, there are various ATPS systems including but not limited to polymer-polymer (e.g., PEG-PVP), polymer-salt (e.g. PEG-salt), and micellar. The first and/or second component comprises a polymer. Polymer includes but is not limited to polyalkylene glycols, such as hydrophobically modified polyalkylene glycols, poly(oxyalkylene)polymers, poly(oxyalkylene)copolymers, such as hydrophobically modified poly(oxyalkylene)copolymers, polyvinyl pyrrolidone (PVP), polyvinyl alcohol, polyvinyl caprolactam, polyvinyl methylether, alkoxylated starches, alkoxylated cellulose, alkyl hydroxyalkyl cellulose, silicone-modified polyethers, and poly N-isopropylacrylamide and copolymers thereof. In another embodiment, the first polymer comprises polyethylene glycol, polypropylene glycol.

In one embodiment, the polymer concentration of the first or second phase is in the range of about 0.01% to about 90% by weight of the total weight of the aqueous solution (w/w). In various embodiments, the polymer solution is selected from a polymer solution that is about 0.01% w/w, about 0.05% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9%) w/w, about 0.95% w/w, or about 1% w/w. In some embodiments, the polymer solution is selected from polymer solution that is about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, and about 50% w/w.

In one embodiment, the first and/or second phase comprises a salt, the salt includes but is not limited to, inorganic salts containing cations such as straight or branched trimethyl ammonium, triethyl ammonium, tripropyl ammonium, tributyl ammonium, tetramethyl ammonium, tetraethyl ammonium, tetrapropyl ammonium and tetrabutyl ammonium, and anions such as sulphate, nitrate, chloride and hydrogen carbonate. In another embodiment, the salt is selected from the group consisting of NaCl, $Na_2SO_4$, potassium citrate, $(NH_4)_2SO_4$, sodium citrate, sodium acetate, sodium cholate and combinations thereof. Other salts, e.g. ammonium acetate, may also be used.

In one embodiment, the total salt concentration is in the range of 0.001 mM to 100 mM. A skilled person in the art will understand that the amount of salt needed to form an aqueous two-phase system will be influenced by molecular weight, concentration and physical status of the polymer.

In various embodiments, the salt phase is selected from a salt solution that is about 0.001% to 90% w/w. In various embodiments, the salt solution is selected from a salt solution that is about 0.01% w/w, about 0.05% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9%) w/w, about 0.95% w/w, or about 1% w/w. In some embodiments, the salt solution is selected from polymer solution that is about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, and about 50% w/w.

In one embodiment, the first and/or the second phase in the ATPS comprises a solvent that is immiscible with water. In some embodiments, the solvent comprises a non-polar organic solvent.

In some embodiments, the solvent comprises an oil. In some embodiments, the solvent is selected from pentane, cyclopentane, benzene, 1,4-dioxane, diethyl ether, dichloromethane, chloroform, toluene and hexane.

In one embodiment, the first phase and/or second phase in the ATPS comprises a micellar solution.

In one embodiment, one phase in the ATPS comprises a micellar solution and the other phase comprises a liquid phase comprising a polymer. In one embodiment, one phase in the liquid phase comprises a micellar solution and the other phase in the liquid phase comprises a salt solution. In one embodiment, one phase comprises a first polymer and the other comprises a second polymer. In one embodiment, the first/second polymer is selected from polyethylene glycol and PVP. In one embodiment, one phase comprises a polymer and the other phase comprises a salt. In some embodiments, one phase comprises PVP and the other phase comprises sodium cholate. In one embodiment, one phase comprises a salt and the other comprises another salt.

In one embodiments, the volume ratios of the first phase to the second phase are in the range of 1:1 to 1:1000. In some embodiments, the ratio of the first phase to the second phase is selected from a ratio of about 1:1, about 1:2, about 1:3, about 1:4, about 1:5, about 1:6, about 1:7, about 1:8, about 1:9, and about 1:10. In some embodiments the ratio of the first phase to the second phase is selected from a ratio of about 1:20, about 1:30, about 1:40, about 1:50, about 1:60, about 1:70, about 1:80, about 1:90, and about 1: 100. In some embodiments the ratio of the first phase to the second phase is selected from a ratio of about 1:200, about 1:300, about 1:400, about 1:500, about 1:600, about 1:700, about 1:800, about 1:900, and about 1:1000.

In one embodiment, the volume ratios of the second phase to the first phase are selected from a ratio of about 1:1, about 1:2, about 1:3, about 1:4, about 1:5, about 1:6, about 1:7, about 1:8, about 1:9, and about 1:10. In some embodiments the ratio of the second phase to the first phase is selected from a ratio of about 1:20, about 1:30, about 1:40, about 1:50, about 1:60, about 1:70, about 1:80, about 1:90, and about 1:100. In some embodiments the ratio of the second phase to the first phase is selected from a ratio of about 1:200, about 1:300, about 1:400, about 1:500, about 1:600, about 1:700, about 1:800, about 1:900, and about 1:1000.

Downstream Processing of the Isolated Analyte

In various embodiments, the present invention can be integrated with a second device at the downstream region of the porous material of said first device, such that the leading fluid within the porous material would transfer into said second device.

In various embodiments, the present invention can be integrated with a second device at the downstream region of the porous material of said first device, such that the leading fluid within the porous material would transfer into said second device. The phase separation behavior modifying agent(s) is/are selected to benefit either directly or indirectly the performance of said second device integrated at the downstream region through any combination of means described in this invention.

Analytes and/or analytes-containing solution obtained by the present invention can be used in conjugation with a wide range of downstream applications such as detection or analysis of the analytes in forensic, diagnostic or therapeutic applications, and laboratory procedures such as sequencing, amplification, reverse transcription, labeling, digestion, blotting procedures and the like. The present invention can improve the performance of downstream characterization or processing of the analytes.

In one embodiment, downstream applications of the analyte include, but are not limited to, any detection, analytical or diagnostic procedures involving the detection or quantification of the purified analyte. In one embodiment, detection, analytical or diagnostic procedures to be coupled with the present invention include but are not limited to any such procedure performed in commercial clinical laboratory, and laboratory procedures such as sequencing, amplification (e.g. PCR, RT-PCR, real-time PCR, and real-time RT-PCR), reverse transcription, labeling, digestion, blotting procedures, ELISA, RIA, immunoassays, enzymatic assays, GC/MS, proteomic-based approach, and the like.

In one embodiment, analyte and/or analytes-containing solution obtained by the present invention can be analyzed by a lateral flow assay (LFA). LFA has a number of desirable characteristics including their ease of use and board applicability to a variety of analytes. However, LFA is generally only capable of providing qualitative results due to its detection limitation. For example, the detection limit of LFA on pathogen (*S. mutans*) is $10^6$ CFU/ml. In the present invention wherein modifying agent is used to improve the phase separation of the ATPS, the detection limit of LFA on *S. mutans* can be improved to as low as $10^4$ CFU/ml amounting to a 100-fold enhancement. Together with the improved concentration fold by 100-fold, the present invention is suited for providing quantitative result in a broader range.

In one embodiment, the partition of the target analyte to the phase of interest can be enhanced by adding modifying agent to the ATPS. In one embodiment, the fold of concentration is improved by 100-fold. The improved partition of the target analyte is also beneficial to increase yield of target analyte.

It may produce a false negative result if the target analyte has extremely low concentration. In one embodiment, due to the increased concentration of the target analyte by adding one or more modifying agent(s) to the ATPS, the detection limit of LFA is improved. As a result, the reproducibility of the test is increased.

In one embodiment, by adding one or more modifying agent(s), phase separation of the ATPS can be induced to occur earlier and /or at a lower concentration of the ATPS components. As a result, efficiency or speed of the entire detection or diagnostic process can be increased significantly.

In various embodiments, the present invention can be used in combination with one or more processes or reagents for the purpose of washing and elution of the analytes retained in the porous matrix, or post-isolation treatment of the retained analytes.

The first or second device is designed to enable manual and/or automated extraction of the first phase solution and/or the second phase solution from the porous material of said first or second device, and the extracted solution is then used for another method or process.

In various embodiments, the present phase separation behavior modifying agent(s) is/are selected to benefit either directly or indirectly the performance of said method or process that uses said extracted phase through any combination of means described in this invention.

In one embodiment, after contacting the analytes containing solution with the ATPS, a washing buffer is applied on the ATPS, once or for multiple times, to wash off non-target analytes or impurities from the porous matrix. Washing buffers may comprise solutions of varying ionic strength, pH values, or contain additives such as detergents. Washing buffers include but are not limited to a solution of 20%-50% ethanol and 20%-50% isopropanol; a solution of about 0.1-4.0 M guanidinium hydrochloride, detergents and up to about 80% ethanol; or a solution of about 80% ethanol.

In one embodiment, target analytes enter the porous matrix of the ATPS and flow from one end to the other end. In one embodiment, target analytes isolated by the present invention are eluted out of the porous matrix using appropriate elution buffers or deionized water. In one embodiment, isolated target analytes are not eluted but stored in the porous matrix for future use. For instance, after the isolation of analytes using the present invention, the porous material (e.g., a paper) containing the target analytes (e.g., a DNA) is dried and stored. In one embodiment, analytes retained on the porous matrix can be eluted for further analysis or treatment. The selection of the elution buffer may depend on the contemplated use of the purified biomarker. Examples of suitable elution buffers for nucleic acid type of analytes includes, but are not limited to, Tris-EDTA (TE) buffer, aqua bidest and PCR buffer. In one embodiment, the purified analyte on porous paper is eluted in a tube containing TE buffer (10 mM TrisCl, 1 mM EDTA solution with pH 7.5), and the purified analyte is recovered in a relatively small volume, e.g., less than 100 µl.

In one embodiment, the present invention provides a device for isolating or concentrating one or more target analytes, the device comprising:
  i) a porous material;
  ii) components capable of forming a first phase solution and a second phase solution of an aqueous two-phase system (ATPS); and
  iii) one or more phase separation behavior modifying agents;
  wherein said components and said phase separation behavior modifying agents are embedded in said porous material, wherein when a solution containing said target analytes flows through said porous material, an aqueous two-phase system comprising said first phase solution and said second phase solution is generated, wherein the separation behavior of the two phase solutions is altered by said phase separation behavior modifying agents, and said target analytes are isolated or concentrated on said porous material, or
  wherein one or more of said components and said phase separation behavior modifying agents are embedded in said porous material, wherein the balance of said components and said phase separation behavior modifying agents are to be mixed with a solution containing said target analytes, thereby forming a mixed solution, wherein when said mixed solution flows through said porous material, an aqueous two-phase system comprising said first phase solution and said second phase solution is generated, wherein the separation behavior of the two phase solutions is altered by said phase separation behavior modifying agents, and said target analytes are isolated or concentrated on said porous material.

In one embodiment, the one or more phase separation behavior modifying agents are present in some regions of the porous material, and not present in other regions of the porous material.

In one embodiment, one or more phase separation behavior modifying agents are evenly distributed on said porous material or present in an increasing amount from one end to the other end of said porous material.

In one embodiment, one or more phase separation behavior modifying agents are present in varying amounts in different regions of the porous material.

In one embodiment, one or more target analytes partition into the first phase solution or the second phase solution, or accumulate at an interface between the first phase solution and the second phase solution.

In one embodiment, the porous material and said components are selected so that said first phase solution and second phase solution flow through the porous material at different rates.

In one embodiment, one or more phase separation behavior modifying agents are selected from the group consisting of:
  a) compounds carrying one or more acidic functional groups;
  b) compounds carrying one or more amine functional groups; and
  c) compounds carrying both hydrophilic and hydrophobic groups.

In one embodiment, the compounds carrying one or more acidic functional groups are selected from the group consisting of saccharides, polysaccharides, sorbates, polysorbates, carboxylates, polycarboxylates, phosphates, polyphosphates, sulfates, polysulfates and polyols.

In one embodiment, said compounds carrying one or more amine functional groups are selected from the group consisting of amines, polyamines, amine salts and polyamine salts.

In one embodiment, the compounds carrying both hydrophilic and hydrophobic groups are selected from the group consisting of lipids, surfactants, nucleic acids, hormones, proteins, and amino acids.

In one embodiment, the phase separation behavior modifying agent is a chaotropic agent. In one embodiment, the phase separation behavior modifying agent is a kosmotropic agent.

In one embodiment, one or more phase separation behavior modifying agents are selected to:

a) reduce fluctuations in the total volume of the first phase solution, the second phase solution, or both during or after phase separation;
b) increase or decrease the total volume of the solution containing said target analytes that undergoes a phase separation;
c) reduce fluctuations in the volume ratio between the first phase solution and the second phase solution; or
d) increase or decrease the volume ratio between the first phase solution and the second phase solution.

In one embodiment, one or more phase separation behavior modifying agents are selected to:
a) reduce fluctuations in the concentrations of one or more components within the first phase solution;
b) reduce fluctuations in the concentrations of one or more components within the second phase solution;
c) increase or decrease the concentration of one or more components within the first phase solution; or
d) increase or decrease the concentration of one or more components within the second phase solution.

In one embodiment, one or more phase separation behavior modifying agents are selected to induce phase separation when the concentrations of said components are not sufficient to induce phase separation without the presence of said modifying agents.

In one embodiment, one or more phase separation behavior modifying agents are selected to:
a) reduce fluctuations in the rate of domain coalescence; or
b) increase or decrease the rate of domain coalescence.

In one embodiment, one or more phase separation behavior modifying agents are selected to:
a) reduce fluctuations in the flow rate of the first phase solution within the porous material;
b) reduce fluctuations in the flow rate of the second phase solution within the porous material;
c) increase the flow rate of the first phase solution within the porous material;
d) decrease the flow rate of the first phase solution within the porous material;
e) increase the flow rate of the second phase solution within the porous material; or
f) decrease the flow rate of the second phase solution within the porous material.

In one embodiment, one or more phase separation behavior modifying agents are selected to:
a) reduce fluctuations in the partitioning of said target analytes between the first phase solution and the second phase solution;
b) increase the partitioning of said target analytes to the first phase solution;
c) decrease the partitioning of said target analytes to the first phase solution;
d) increase the partitioning of said target analytes to the second phase solution; or
e) decrease the partitioning of said target analytes to the second phase solution.

In one embodiment, the device is further integrated with a second device such that a leading fluid within the porous material would transfer into said second device.

In one embodiment, the present invention also provides a method of using the device for isolating or concentrating one or more target analytes from a sample solution.

In one embodiment, the target analytes isolated or concentrated on the porous material are extracted to generate an extract solution to be subsequently used in another method or process.

Throughout this application, it is to be noted that the transitional term "comprising", which is synonymous with "including", "containing" or "characterized by", is inclusive or open-ended, and does not exclude additional, un-recited elements or method steps.

This invention will be better understood by reference to the examples which follow. However, one skilled in the art will readily appreciate that the examples provided are merely for illustrative purposes and are not meant to limit the scope of the invention which is defined by the claims following thereafter.

EXAMPLES

Example 1

Using Dextran to Reduce Volume Ratio Fluctuations in a Device for Detecting Pathogens (*S. mutans*) in Patient Samples Preparation of sample pad for LFA: Fiberglass porous paper sheets were cut into 0.5 cm×4 cm rectangles. The formulated ATPS components, 20% (w/w) PVP and 18.5% (w/w) sodium cholate were pipetted onto the fiberglass porous paper. The above porous papers with ATPS were then dried in a lyophilizer for 2 hours first. 10% (w/w) dextran was then pipetted onto the fiberglass porous paper as the phase separation behavior modifying agent onto the paper segments. PEG solution (in DI $H_2O$) was added to each porous material. 50 µl of a Tris-buffered solution containing 2% bovine serum albumin (BSA), and 0.1% PEG, 20 mM Tris pH 7.5 respectively) was added immediately adjacent to the first solution.

The above porous papers with ATPS and the phase separation behavior modifying agent were then dried in a lyophilizer for 2 hours. The ATPS within porous papers were then placed in an indicator-containing (colloidal gold) buffer solution in PBS (overall pH 7.4), resulting in capillary action-mediated flow. The dextran solution is applied to one end of the porous paper so that it creates a gradient concentration along the diffusion direction:

The purpose of the dextran (phase separation behavior modifying agent) is to stabilize (i.e. reduce fluctuations) the volume ratio of the ATPS during variable fluid flow rates, making the test more robust. The gradient of dextran is important so that the volume ratio is still large enough by the time the fluid flow reaches the end of the porous material. Place paper segments under low pressure vacuum for 2 hours to dehydrate.) Multiple layers of porous papers with the dehydrated ATPS components and phase separation behavior modifying agent are assembled together.

Preparation of LFA test strip: 1) anti-*S. mutans* antibody at a concentration of 1 mg/mL, and 2) Protein (Bovine Serum Albumin, BSA) at a concentration of 0.2 mg/ml were added on the test strip. Colloidal gold nanoparticles were conjugated to the anti-*S. mutans* antibody as directed by manufacturer instructions. This conjugate was then dried onto the conjugating pad material using a lyophilizer. The absorbent pad consisted of untreated paper.

The LFA test strip was integrated with sample pad, i.e., the porous device/component with the dehydrated ATPS components and the phase separation behavior modifying agent. The porous device/component and the LFA component are placed into an appropriate housing such that the components are held in place.

Detection using LFA: The fiberglass porous paper dehydrated with ATPS components and the phase separation behavior modifying agent, a blank paper (without ATPS or modifying agent) and a control paper (ATPS without modifying agent) were dipped in a same solution of saliva, which was in a PBS buffer solution at pH 7.4. After the sample solution flowed through the porous material and through the LFA test for 2 min, another 2 mins was needed to develop the test results. The presence or absence of a test line by visual observation was used to determine the results of the diagnostic. The result is summarized in Table 1 below:

TABLE 1

| | Intensity of test line | | |
|---|---|---|---|
| | ATPS with modifying agent | Control Paper (ATPS without modifying agent) | Blank paper (without ATPS or modifying agent) |
| Intensity of test line | 10x | 3x | 1x |

Table 1 clearly shows that adding phase separation behavior modifying agents to ATPS can increase the intensity of test line, indicating that the concentration of the target analyte is increased significantly.

Example 2

Using Polysorbate and Sucrose to Increase Food Allergen (Lupine) Partition in a Detecting Device Preparation of sample pad for LFA: Fiberglass porous paper sheets were cut into 0.5 cm×4 cm rectangles. The formulated ATPS components, 20% (w/w) PVP and 18.5% (w/w) sodium cholate were pipetted onto the fiberglass porous paper. 5% (w/w) polysorbate and 5% (w/w) sucrose were pipetted onto the porous fiberglass paper as the phase separation behavior modifying agent. PEG solution (in DI $H_2O$) was added to each porous material. 50 μl of a Tris-buffered solution containing 2% bovine serum albumin (BSA), and 0.1% PEG, 20 mM Tris pH 7.5 respectively) was added immediately adjacent to the first solution.

The above porous papers with dehydrated ATPS components and the phase separation behavior modifying agent were then dried in a lyophilizer for 1 hour. The ATPS-dehydrated porous papers were then placed in an indicator-containing (colloidal gold) buffer solution in PBS (overall pH 7.4), resulting in capillary action-mediated flow. The polysorbate and sucrose were applied so that it creates an even distribution of the components on the porous material. Multiple layers of porous papers with the dehydrated ATPS components and the phase separation behavior modifying agent were assembled together.

The purpose of the polysorbate and sucrose is to increase food allergen target partitioning into the first phase. Then place paper segments in an oven at 37 degrees Celsius for 28 hours to dehydrate.

Preparation of LFA test strip: 1) anti-lupine antibody at a concentration of 1 mg/ml, and 2)

Protein (Bovine Serum Albumin, BSA) at a concentration of 0.2 mg/ml were added on the test strip. Colloidal gold nanoparticles were conjugated to anti-lupine antibody as directed by manufacturer instructions. This conjugate was then dried onto the conjugating pad material using a lyophilizer. The absorbent pad consisted of an untreated paper.

The LFA test strip was first integrated with the sample pad, i.e., the porous material for tests food allergen (lupine) and then integrated with a food matrix grinder/processor. The integrated device should be assembled such that the flow of the sample solution will go from the food matrix grinder/processor down into the porous component, then flow forward further through the porous material where it will resolubilize the ATPS components and the phase separation behavior modifying agents which will induce phase separation and facilitate food allergen partition into the leading first phase, and finally into the LFA component. All of the components were integrated into the appropriate cassette/housing to hold the components in place.

Detection of food allergen using LFA. The food samples of interest were placed into the food matrix grinder/processor portion of the device. The food matrix grinder/processor was manually operated to break down the food matrix. The fiberglass porous paper dehydrated with ATPS components and the phase separation behavior modifying agent, a blank paper (without ATPS or modifying agent) and a control paper (ATPS without modifying agent) were dipped in food matrix sample in a PBS buffer solution at pH 7.4. After the sample solution flowed through the remaining device for 2 min, another 2 min was needed to develop the test results. The presence or absence of a test line by visual observation was used to determine the results of the diagnostic. The result is summarized in Table 2 below:

TABLE 2

| | Intensity of test line | | |
|---|---|---|---|
| | ATPS with modifying agent | Control Paper (ATPS without modifying agent) | Blank paper (without ATPS or modifying agent) |
| Intensity of test line | 8x | 2x | 1x |

Table 2 clearly shows that adding phase separation behavior modifying agents to ATPS can increase the intensity of test line, indicating that the concentration of the target analyte is increased significantly.

Example 3

Using Potassium Phosphate to Increase Total Phase Separation Volume in a Device for Sample Solution Purification and DNA Amplification Porous hydrogel material was cut into cylindrical shape with dimensions of 2 cm radius and 6 cm height. The porous hydrogel component was integrated into an appropriate cassette/housing. The device can expose the bottom of the hydrogel as well as the top of the hydrogel.

The ATPS components, 20% (w/w) PVP and 18.5% (w/w) sodium cholate, 10% (w/w) potassium phosphate as the phase separation behavior modifying agent were mixed with a blood sample solution containing the DNA segments of interest in a PBS buffer solution at pH 7.4. The purpose of the potassium phosphate is to induce macroscopic phase separation at an earlier point (more upstream) during the flow of solutions through the porous material, resulting in a great volume undergoing phase separation and a higher volume of solution that is able to be collected at the end of the process. The final volume should be about 120% of the volume that the hydrogel can hold. The sample solution was placed in an open container or tube that can hold the tapered porous device in an upright position. A blank hydrogel material (without ATPS components or modifying agent) and a control hydrogel material (ATPS without modifying agent) were used for comparison.

The bottom and the top of the device were opened to expose the bottom and top of the tapered porous hydrogel. The device was placed into the mixture of sample solution and ATPS components. The liquid of the mixture is in contact with the bottom of the porous hydrogel.

Extraction of sample solution: After the solution flowed to the top of the porous hydrogel for 2 min, the purified sample solution was extracted by pipetting it out of the top region of the porous hydrogel. The extracted sample solution is then ready for DNA amplification. The yield of purified sample was analyzed by UV-Vis spectrophotometry. The result is summarized in Table 3 below.

TABLE 3

Fold of concentration of DNA using the present invention

| Test | ATPS with modifying agent | Control hydrogel (ATPS without modifying agent) | Blank hydrogel (without ATPS or modifying agent) |
|---|---|---|---|
| Yield of DNA (%) | 98% | 50% | 7% |
| Fold of Concentration of DNA | 100-fold | 50-fold | 1-fold |

What is claimed is:

1. A device for isolating or concentrating one or more target analytes, the device comprising:
   i) a porous material;
   ii) components capable of forming a first phase solution and a second phase solution of an aqueous two-phase system (ATPS); and
   iii) one or more phase separation behavior modifying agents;
   wherein said components and said phase separation behavior modifying agents are embedded in said porous material, wherein when a solution containing said target analytes flows through said porous material, an aqueous two-phase system comprising said first phase solution and said second phase solution is generated, wherein the separation behavior of the two phase solutions is altered by said phase separation behavior modifying agents, and said target analytes are isolated or concentrated on said porous material, or
   wherein one or more of said components and said phase separation behavior modifying agents are embedded in said porous material, wherein the balance of said components and said phase separation behavior modifying agents are to be mixed with a solution containing said target analytes, thereby forming a mixed solution, wherein when said mixed solution flows through said porous material, an aqueous two-phase system comprising said first phase solution and said second phase solution is generated, wherein the separation behavior of the two phase solutions is altered by said phase separation behavior modifying agents, and said target analytes are isolated or concentrated on said porous material;
   wherein said one or more phase separation behavior modifying agents are present in varying amounts in different regions of the porous material; and
   wherein the phase separation behavior modifying agents are compounds which can induce, stabilize and/or promote phase separation of the ATPS by changing the temperature, pH, salt concentration, hydrophobicity/hydrophilicity, surface tension, and/or ionic strength of said components.

2. The device of claim 1, wherein said one or more phase separation behavior modifying agents are present in an increasing amount from one end to the other end of said porous material.

3. The device of claim 1, wherein said one or more target analytes partition into the first phase solution or the second phase solution, or accumulate at an interface between the first phase solution and the second phase solution.

4. The device of claim 1, wherein the porous material and said components are selected so that said first phase solution and second phase solution flow through the porous material at different rates.

5. The device of claim 1, wherein said one or more phase separation behavior modifying agents are selected from the group consisting of:
   a) compounds carrying one or more acidic functional groups;
   b) compounds carrying one or more amine functional groups;
   c) compounds carrying both hydrophilic and hydrophobic groups;
   d) chaotropic agents; and
   e) kosmo tropic agents.

6. The device of claim 5, wherein said compounds carrying one or more acidic functional groups are selected from the group consisting of saccharides, polysaccharides, sorbates, polysorbates, carboxylates, polycarboxylates, phosphates, polyphosphates, sulfates, poly sulfates and polyols.

7. The device of claim 5, wherein said compounds carrying one or more amine functional groups are selected from the group consisting of amines, polyamines, amine salts and poly amine salts.

8. The device of claim 5, wherein said compounds carrying both hydrophilic and hydrophobic groups are selected from the group consisting of lipids, surfactants, nucleic acids, hormones, proteins, and amino acids.

9. The device of claim 1, wherein said one or more phase separation behavior modifying agents are selected to:
   a) reduce fluctuations in the total volume of the first phase solution, the second phase solution, or both during or after phase separation;
   b) increase or decrease the total volume of the solution containing said target analytes that undergoes a phase separation;
   c) reduce fluctuations in the volume ratio between the first phase solution and the second phase solution; or
   d) increase or decrease the volume ratio between the first phase solution and the second phase solution.

10. The device of claim 1, wherein said one or more phase separation behavior modifying agents are selected to:
    a) reduce fluctuations in the concentrations of one or more components within the first phase solution;
    b) reduce fluctuations in the concentrations of one or more components within the second phase solution;
    c) increase or decrease the concentration of one or more components within the first phase solution; or
    d) increase or decrease the concentration of one or more components within the second phase solution.

11. The device of claim 1, wherein said one or more phase separation behavior modifying agents are selected to induce phase separation when the concentrations of said components are not sufficient to induce phase separation without the presence of said modifying agents.

12. The device of claim 1, wherein said one or more phase separation behavior modifying agents are selected to:
   a) reduce fluctuations in the rate of domain coalescence; or
   b) increase or decrease the rate of domain coalescence.

13. The device of claim 1, wherein said one or more phase separation behavior modifying agents are selected to:
   a) reduce fluctuations in the flow rate of the first phase solution within the porous material;
   b) reduce fluctuations in the flow rate of the second phase solution within the porous material;
   c) increase the flow rate of the first phase solution within the porous material;
   d) decrease the flow rate of the first phase solution within the porous material;
   e) increase the flow rate of the second phase solution within the porous material; or
   f) decrease the flow rate of the second phase solution within the porous material.

14. The device of claim 1, wherein said one or more phase separation behavior modifying agents are selected to:
   a) reduce fluctuations in the partitioning of said target analytes between the first phase solution and the second phase solution;
   b) increase the partitioning of said target analytes to the first phase solution;
   c) decrease the partitioning of said target analytes to the first phase solution;
   d) increase the partitioning of said target analytes to the second phase solution; or
   e) decrease the partitioning of said target analytes to the second phase solution.

15. The device of claim 1, wherein said device is further integrated with a second device such that a leading fluid within the porous material would transfer into said second device.

16. A method of using the device of claim 1 for isolating or concentrating one or more target analytes from a sample solution.

17. The method of claim 16, wherein the target analytes isolated or concentrated on the porous material are extracted to generate an extract solution to be subsequently used in another method or process.

18. The device of claim 1, wherein the one or more phase separation behavior modifying agents is selected from the group consisting of sucrose, potassium phosphates, dextran, Tween-20 and Triton-X114.

19. The device of claim 1, wherein the phase separation behavior modifying agent is dextran.

20. The device of claim 1, wherein the phase separation behavior modifying agent is 10% (w/w) dextran, and the aqueous two-phase system (ATPS) components comprise 20% (w/w) PVP and 18.5%(w/w) sodium cholate.

* * * * *